United States Patent
Gabara et al.

(10) Patent No.: US 7,024,000 B1
(45) Date of Patent: Apr. 4, 2006

(54) ADJUSTMENT OF A HEARING AID USING A PHONE

(75) Inventors: Thaddeus John Gabara, Murray Hill, NJ (US); Scott Wayne McLellan, Albany Township, PA (US); David L. Smith, Hummelstown, PA (US)

(73) Assignee: Agere Systems Inc., Allentown, PA (US)

( * ) Notice: Subject to any disclaimer, the term of this patent is extended or adjusted under 35 U.S.C. 154(b) by 963 days.

(21) Appl. No.: 09/589,391

(22) Filed: Jun. 7, 2000

(51) Int. Cl.
*H04B 29/00* (2006.01)
*A61B 5/00* (2006.01)
*H04M 11/00* (2006.01)

(52) U.S. Cl. .......................... 381/60; 600/559; 379/52

(58) Field of Classification Search .................. 381/60; 73/585; 600/559; 379/52, 102.01, 102.02, 379/102.07
See application file for complete search history.

(56) References Cited

U.S. PATENT DOCUMENTS

| | | | | |
|---|---|---|---|---|
| 4,284,847 A | * | 8/1981 | Besserman | 73/585 |
| 5,226,086 A | * | 7/1993 | Platt | 381/58 |
| 5,479,522 A | | 12/1995 | Lindemann et al. | 381/68.2 |
| 5,825,894 A | | 10/1998 | Shennib | 381/60 |
| 5,835,611 A | | 11/1998 | Kaiser et al. | 381/321 |
| 5,852,668 A | | 12/1998 | Ishige et al. | 381/312 |
| 5,870,481 A | | 2/1999 | Dymond et al. | 381/60 |
| 5,923,764 A | | 7/1999 | Shennib | 381/60 |
| 6,086,541 A | * | 7/2000 | Rho | 600/559 |
| 6,118,877 A | * | 9/2000 | Lindemann et al. | 381/60 |
| 6,212,496 B1 | * | 4/2001 | Campbell et al. | 704/221 |
| 6,522,988 B1 | * | 2/2003 | Hou | 702/122 |
| 6,549,633 B1 | * | 4/2003 | Westermann | 381/312 |
| 6,741,712 B1 | * | 5/2004 | Bisgaard | 381/312 |

\* cited by examiner

*Primary Examiner*—Vivian Chin
*Assistant Examiner*—Devona E Faulk

(57) ABSTRACT

A system and method for using a telephone to reconfigure or readjust the performance characteristics of a hearing aid or to check whether a user has a hearing problem. The telephone is used to generate one or more frequency tests covering the audible spectrum using a DSP contained in the phone, an external computer and/or a hearing aid. The keypad of the phone or keyboard of an attached computer is used as a feedback mechanism. The generated frequencies can be used to test the hearing of a user and the quality (or fit) of a hearing aid while being worn by the user. A local memory may be used to store the results of the tests for future reference or for transmission over the network for analysis at a later time. Once the hearing response of a user wearing the hearing aid has been measured, an updated compensation configuration (audiogram) can be downloaded into the hearing aid via an infra-red link, via a physical connection or a direct audio transmission from the telephone to the DSP in the hearing aid.

45 Claims, 3 Drawing Sheets

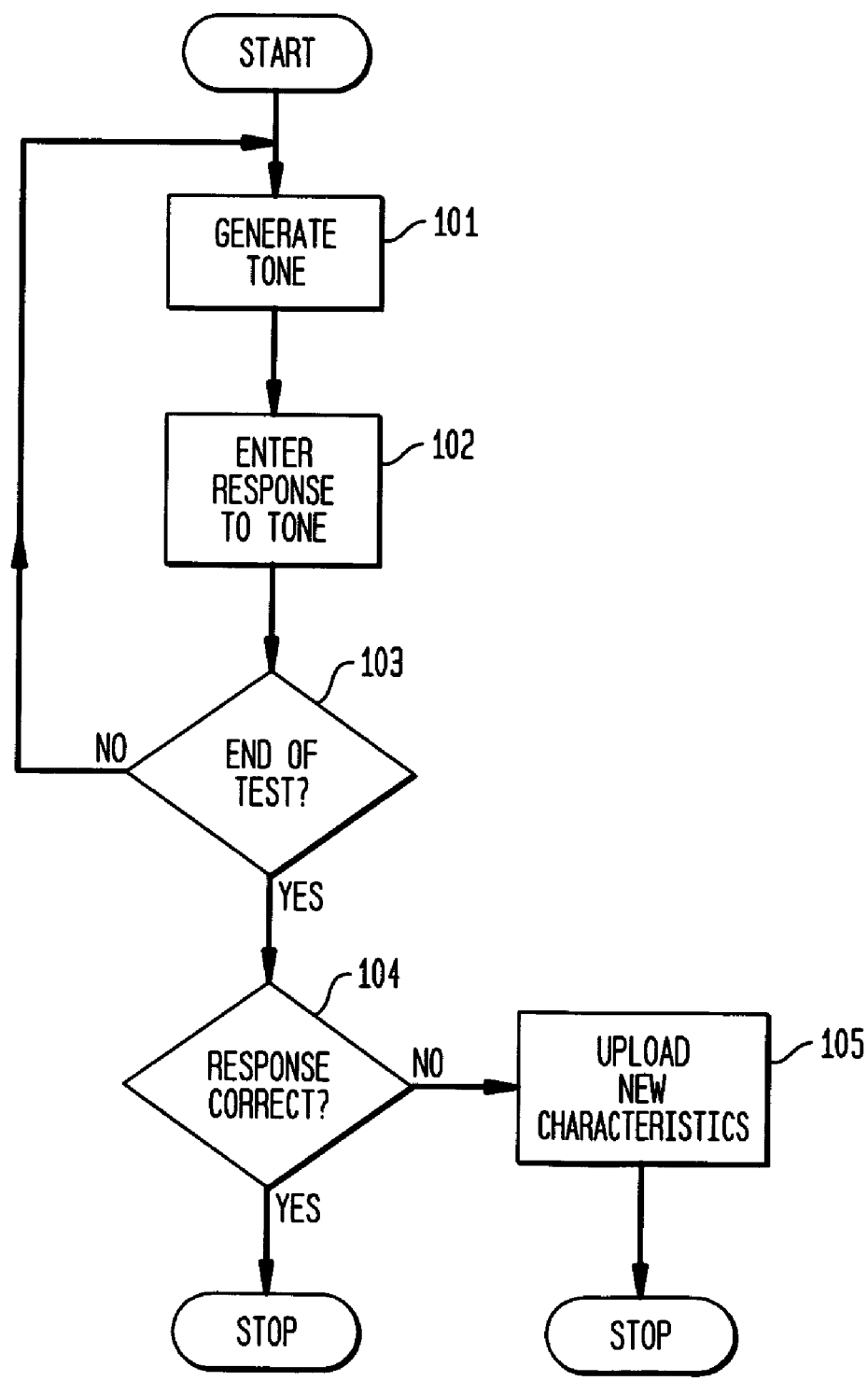

ADJUSTMENT OF A HEARING AID USING A PHONE

BACKGROUND OF THE INVENTION

1. Field of the Invention

The present invention generally relates to the field of hearing aids and, more particularly, to the use of an existing phone to automatically reconfigure or readjust the performance of a hearing aid.

2. Description of the Related Art

The human auditory system processes sounds from a complex 3-dimensional space via the external, middle, and inner ear, as well as via the complex neural pathways that lead to the auditory cortex within the brain. A measurable hearing loss, due to various conductive, sensorineural or central auditory disorders, affects a significant percentage of the human population, particularly elderly persons. Rehabilitation via hearing aids remains the only viable option for those types of hearing impairments that cannot otherwise be medically treated or surgically alleviated.

Conventional hearing aids are analog or digital devices which filter and amplify sound. The frequency response of the filter can be configured to compensate for the frequency-dependent hearing loss of particular users, e.g., as determined by an audiogram. More sophisticated hearing aids can compress the dynamic range of detected sounds amplifying softer sounds below the threshold of hearing while maintaining loud sounds at their usual levels so that they do not exceed the threshold of discomfort. This compression of dynamic range may be performed separately in different frequency bands.

The custom configuration of a hearing aid, typically performed by an audiologist or hearing aid dispenser, involves selecting the frequency response of the aid as a function of a user's audiogram. However, there are a large number of different programming possibilities which result from the number of available hearing aid types and the many hearing aid parameters that can be varied by control elements or by programming, including elements such as frequency response (for example, edge/shift edge steepness in the base and treble range), gain, cut-off point of the Automatic Gain Control ("AGC") peak clipping, etc. The large number of programming possibilities has resulted in the situation where the time expenditure required to run through the numerous possibilities to arrive at an optimum adaptation is no longer justifiable.

Typically, an audiologist or hearing aid dispenser matches the performance characteristics of a conventional hearing aid to the hearing characteristics of a user before delivering the hearing aid to the user. In particular, the audiologist or hearing aid dispenser measures the hearing characteristics of the user, e.g., during an office visit and generates an audiogram representing the measured hearing characteristics. Next, the provider fits the device characteristics to the audiogram. This is typically performed after the customer has left because of the length of time involved. Finally, the adjusted hearing aid is delivered to the user.

Due to the effects of aging or other environmental factors, a person's quality of hearing may vary over time. As a result, a customized hearing aid may require periodic adjustments to take into account changes in the user's hearing characteristics. This adjustment requires the user to remove and return the hearing aid for refitting or to travel to the audiologist or hearing aid dispenser where the fitting process can be performed. Both situations entail a considerable inconvenience, depending on where the user and the audiologist or hearing aid dispenser are located. Furthermore, if the user mails the hearing aid to the audiologist or hearing aid dispenser for fitting, the user will be without their hearing aid while the fitting is being performed. Moreover, without having the user present during the fitting, at best the fitting will be an approximation of the user's hearing characteristics limited by the accuracy of the audiogram.

Accordingly, there is a need and desire to minimize the drawbacks associated with adjusting the hearing aid to compensate for changes over time in the hearing characteristics of a user.

SUMMARY OF THE INVENTION

The present invention is a system and method for using a telephone to reconfigure or readjust the performance characteristics of a hearing aid or to check whether a user has a hearing problem. A conventional telephone network connection has a bandwidth of 300 Hz to 4 KHz. However, many telephones contain components which generate frequencies which exceed this narrow bandwidth. In particular, many modern telephones contain a sophisticated digital signal processor (DSP) which can be programmed to perform operations, such as generating tones or frequencies ranging from 300 Hz to 20,000 Hz, for use in performing audio tests.

In accordance with the present invention, the telephone is used to generate one or more frequency tests covering the audible spectrum using the DSP contained in the phone and/or an external computer. Alternatively, the DSP may be located in the hearing aid and is controlled by a digital link from the telephone or external computer by an acoustical, infra red, RF or physical link. The keypad of the phone may be used as a feedback mechanism. The generated frequencies can be used to test the hearing of a user and the quality (or fit) of a hearing aid while being worn by the user.

A local memory may be used to store the results of the tests for future reference or for transmission over the telephone network for analysis at a later time. Once the hearing response of a user wearing the hearing aid has been measured, an updated compensation configuration (audiogram) can be downloaded into the hearing aid via a wireless link, such as an infra-red, RF, or acoustic link, or via a physical connection, for example, a modem connected to the telephone network.

Advantageously, the testing may be performed at a user's home and the results automatically sent to the audiologist or hearing dispenser for later analysis. Moreover, a history of measurements may be used to indicate additional problems in the hearing of a user.

BRIEF DESCRIPTION OF THE DRAWINGS

The foregoing and other advantages and features of the invention will become more apparent from the detailed description of the preferred embodiments of the invention given below with reference to the accompanying drawings in which:

FIG. 5 is a flow chart which illustrates the steps of the method according to the invention.

DETAILED DESCRIPTION OF THE PREFERRED EMBODIMENTS

Figure 1:
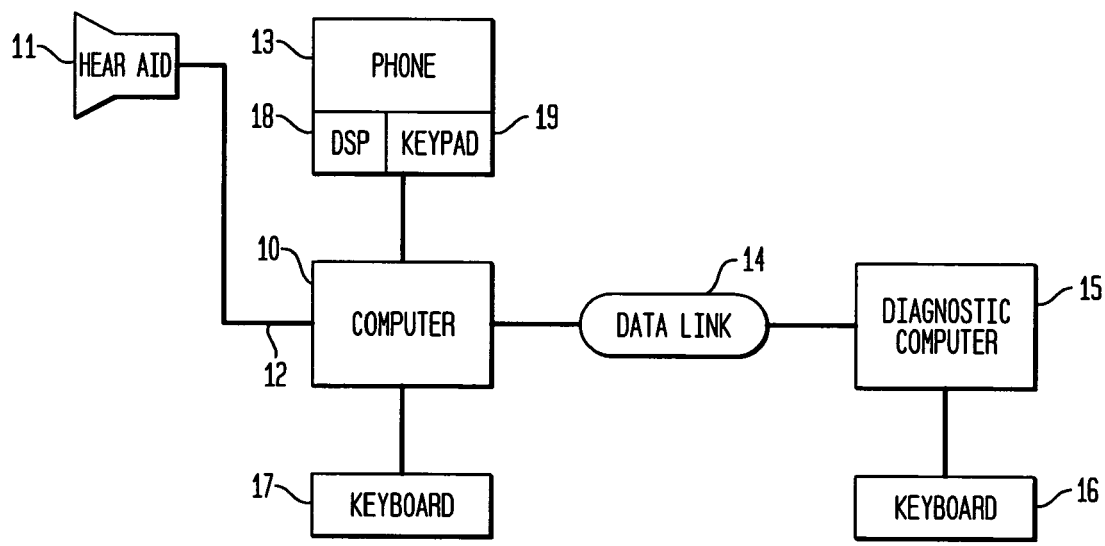
FIG. 1 is an illustration of a system for implementing the method according to the invention.

An embodiment of the invention is shown in FIG. 1. In the illustrated embodiment, the system comprises a programming device, such as a personal computer 10, which is equipped with a keyboard 17 or other input device. The computer 10 is connected to a hearing aid 11, whose transmission characteristics are to be adapted by a data link 12, such as a hard wire link, a wireless link such as an infra-red, RF, magnetic, or acoustic link (not shown). The computer 10 is additionally connected to a telephone 13 which contains a DSP 18. Keyboard 17 is used by a user of the system to implement responses to inputs from an audiologist or hearing aid dispenser. Alternatively, the telephone keypad 19 can be used as a user input device.

In communication with the computer 10 via a remote data link 14 (a direct dial-up connection via a modem, for example) is a diagnostic computer 15 having a keyboard 16 for inputting test tone commands from the audiologist or hearing aid dispenser. In accordance with the invention, an audiologist or hearing aid dispenser sends a command (for example, a DTMF tone which indicates pitch, volume and duration) for transmission via a diagnostic computer 15 at a first location. The command is then transmitted over the remote data link 14 to the test computer 10 at a second location. This command is sent from the test computer 10 to a DSP 18 in a telephone 13 while the user is listening to the phone. A test tone is then generated from the DSP 18 based on the output command and is received by the user of the telephone 13 who is wearing the hearing aid. In response to the received tone, the user then enters a response to the test tone on the keyboard 17. This response is transmitted back to the diagnostic computer 15 over the remote data link 14, where a test using a computer program is performed to determine whether or not the user correctly responded to the generated tone. This can be repeated at a number of frequencies over the audio range.

If it is determined that the user did not respond to the tones correctly, an updated compensation configuration (audiogram) is calculated in computer 15 and is downloaded into the hearing aid by the audiologist. Alternatively, an updated compensation configuration (audiogram) may be automatically downloaded using the computer program. The hearing test is performed across the expanded frequency spectrum in the range from 300 Hz to 20 KHz. In this manner, the quality (or fit) of a hearing aid, while being worn by a user, may be tested.

Instead of using local the computer 10, the entire testing operation can be set up using phone 13 connected to the data link 14, which may be a telephone line. The computer 15 sends messages over the phone line directly to the DSP 18 in the phone. This causes it to respond by creating a series of tones over the audio spectrum. The user of the hearing aid 11 responds to these tones by using the keypad 19 on the phone. The responses are sent to computer 15 where they are stored for later use by the audiologist.

The information thus gathered can be stored in the diagnostic computer 15 for later retrieval by an audiologist or hearing aid dispenser. Alternatively, the test may be performed at the user end of the network 14 using only the computer 10 in an off-line manner. The preceding tests are performed using algorithms which are stored in the computer 10 and diagnostic computer 15. The hearing aid 11 may also be removed from the ear of the user and manually adjusted.

Figure 2:
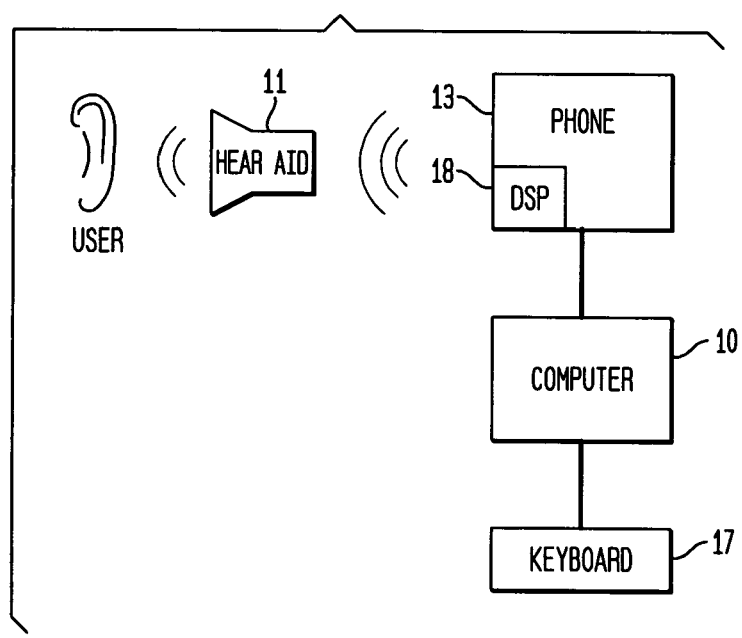
FIG. 2 is an illustration of a closed loop system for implementing the method according to the invention.

An alternative embodiment of the invention is shown in FIG. 2. In this case, the hearing test is performed in a closed loop system which comprises the telephone 13 containing the DSP 18, the hearing aid 11 and computer 10. Here, the computer 10 is shown as being external to the telephone 13. However, in the present embodiment, the computer 10 may also be integrated into the telephone 13. To perform the hearing test, commands are sent from the computer 10 to the DSP 18. In response to the commands, the DSP 18 generates frequency tones which a user listens to. A hearing test is administered to the user across the expanded frequency spectrum in the range from 300 to 20 kilohertz. Responses to the test tones are input on the keyboard (not shown) of the telephone 13 or on the keyboard of the computer 10. Once the user has completed the test, the results can be stored for subsequent diagnosis by an audiologist or hearing aid dispenser.

Figure 3:
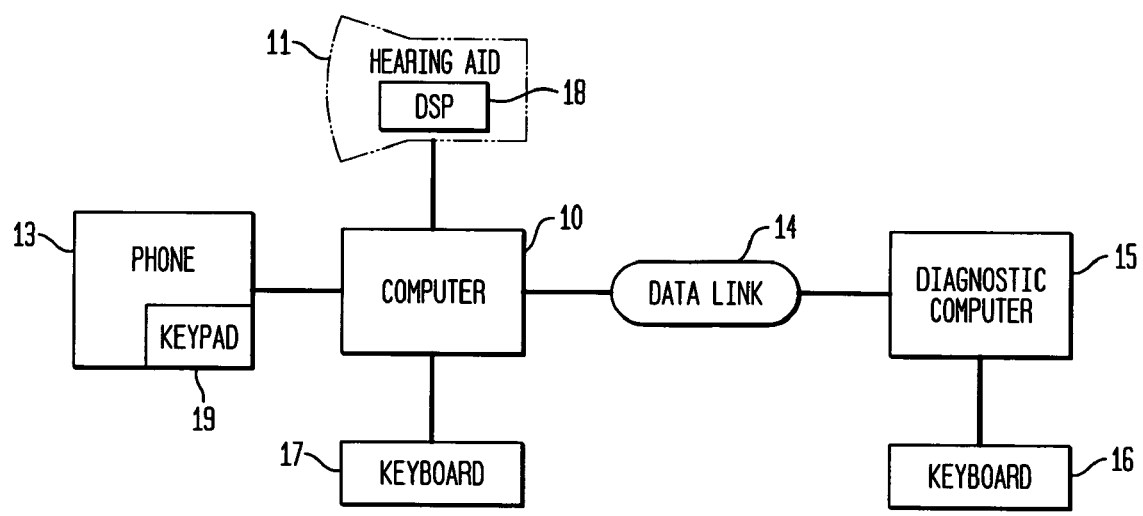
FIG. 3 is an illustration of the system of FIG. 1 with a DSP located in a hearing aid.
Figure 4:
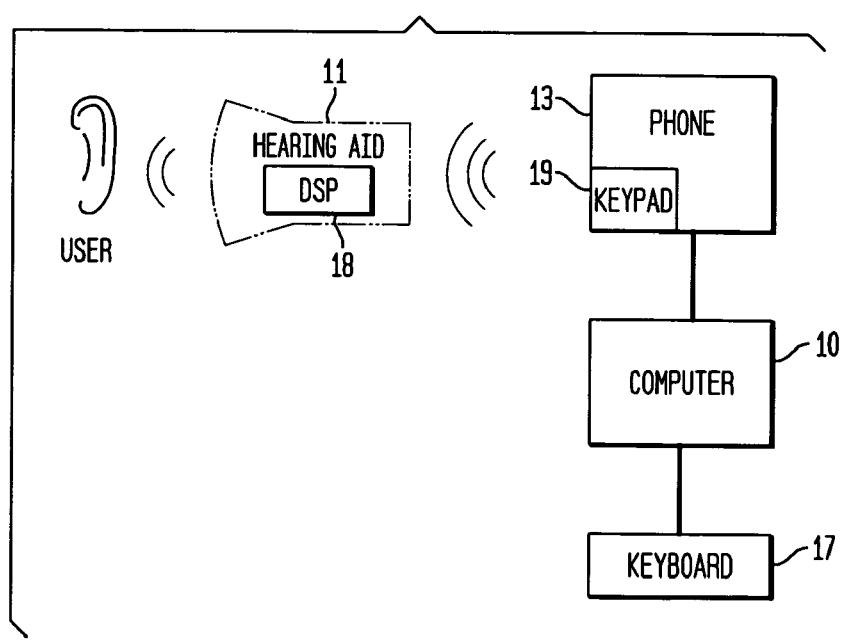
FIG. 4 is illustration of the closed loop system of FIG. 2 with the DSP located in the hearing aid.

In the present invention, as shown in FIG. 3 and FIG. 4, the DSP 18 may be located in the hearing aid 11 (instead of, or in conjunction with, the DSP 18 to in the telephone 13). In this configuration, the hearing test is performed in the manner described previously. However, the commands are sent to the DSP 18 via the telephone 13 in FIG. 4 or computer 10 in FIG. 3. In response to the commands, the DSP 18 then generates the frequency tones which the user wearing the hearing aid 11 listens to. The hearing test is administered to the user across the expanded frequency spectrum in the range from 300 to 20 kilohertz. Responses to the test tones are input on the key pad 19 of the telephone 13 or on the keyboard 17 of the computer 10. As before, once the user has completed the test, the results can be stored for subsequent diagnosis by an audiologist or hearing aid dispenser.

FIG. 5 is a flowchart depicting the steps of the method according to the invention. In a first step 101, an audiologist or a hearing aid dispenser generates a tone which is transmitted over a network 14. On the opposite end of the network, in step 102, a user wearing the hearing aid enters a response to the generated frequency tone. Steps 101 through 103 are interactively repeated until a hearing test along the entire expanded range of frequencies has been performed. In step 104, the responses entered by the user are checked to determine whether or not they are appropriate responses. If the responses to the generated tones are correct, then the process is terminated. On the other hand, if any of the inputted responses are incorrect, then in step 105 a new compensation configuration is computed and uploaded into the hearing aid 11. In this manner, the hearing aid is adjusted such that a custom fit based on the present hearing characteristics of the user is achieved.

Although the invention has been described and illustrated in detail, it is to be clearly understood that the same is by way of illustration and example, and is not to be taken by way of limitation. The spirit and scope of the present invention are to be limited only by the terms of the appended claims.

What is claimed is:

1. A method for remotely adjusting a hearing aid of a user, comprising the steps of:

generating a command via a first computer at a first location;

transmitting the command to a second computer at a second location over a remote data link;

sending the command from the second computer to a digital signal processor in the hearing aid as a DTMF tone;

outputting a test tone from the digital signal processor based on the command to a user of a telephone wearing the hearing aid;

receiving a user response to the test tone over the remote data link; and adjusting the hearing aid based on the user response to the test tone, wherein:

said adjusting step comprises the steps of:
  transmitting the user response to the first computer over the remote data link;
  retrieving a stored audiogram from memory based on an accuracy of the response; and
  uploading the audiogram into the hearing aid of the user over the remote data link; and
said audiogram is a compensation curve for adjusting performance characteristics of the hearing aid based on the user response.

2. The method of claim 1, wherein said receiving step comprises inputting a response to the command into the second computer via a keyboard attached to the computer.

3. The method of claim 1, wherein said receiving step comprises inputting a response to the command via a key pad on the telephone.

4. A method for adjusting a hearing aid of a user, comprising the steps of:
  generating a command via a computer;
  sending the command to a digital signal processor in the hearing aid as a DTMF tone;
  outputting a test tone from the digital signal processor based on the command to the user of a telephone wearing the hearing aid;
  receiving a response to the test tone by the user;
  storing the response to the test tone by the user in the computer;
  retrieving a stored audiogram from memory based on an accuracy of the stored response; and
  uploading the audiogram into the hearing aid of the user.

5. The method of claim 4, wherein said receiving step comprises inputting a response to the command into the computer via a keyboard attached to the computer.

6. The method of claim 4, wherein said receiving step comprises inputting a response to the command via a keypad on the telephone.

7. The method of claim 4, wherein said audiogram is a compensation curve for adjusting performance characteristics of the hearing aid based on the user response.

8. The method of claim 4, wherein the command is generated by a first computer at a first location and is received by a second computer at a second location, and said second computer sends the command to the digital processor.

9. The method of claim 4, wherein the step of sending the command to the digital signal processor is by a wireless link.

10. A method for remotely adjusting a hearing aid of a user, comprising the steps of:
  generating a command via a first computer at a first location;
  transmitting the command to a second computer at a second location over a remote data link;
  sending the command from the second computer to a digital signal processor in the hearing aid as a DTMF tone;
  outputting a test tone from the digital signal processor based on the command to a user of a telephone wearing the hearing aid;
  receiving a user response to the test tone over the remote data link; and
  adjusting the hearing aid based on the user response to the test tone, wherein said receiving step comprises inputting a response to the command into the second computer via a keyboard attached to the computer.

11. A method for remotely adjusting a hearing aid of a user, comprising the steps of:
  generating a command via a first computer at a first location;
  transmitting the command to a second computer at a second location over a remote data link;
  sending the command from the second computer to a digital signal processor in the hearing aid as a DTMF tone;
  outputting a test tone from the digital signal processor based on the command to a user of a telephone wearing the hearing aid;
  receiving a user response to the test tone over the remote data link; and
  adjusting the hearing aid based on the user response to the test tone, wherein said adjusting step comprises the steps of:
    transmitting the user response to the first computer over the remote data link;
    determining an accuracy of the user response;
    retrieving a stored audiogram from memory based on the accuracy of the response; and
    uploading the stored audiogram into the hearing aid of the user over the remote data link.

12. A method for adjusting a hearing aid of a user, comprising the steps of:
  generating a command via a computer;
  sending the command to a digital signal processor in the hearing aid as a DTMF tone;
  outputting a test tone from the digital signal processor based on the command to the user of a telephone wearing the hearing aid;
  receiving a response to the test tone by the user; and
  storing the response to the test tone by the user in the computer, wherein said receiving step comprises inputting a response to the command into the computer via a keyboard attached to the computer.

13. A method for adjusting a hearing aid of a user, comprising the steps of:
  generating a command via a computer;
  sending the command to a digital signal processor in the hearing aid as a DTMF tone;
  outputting a test tone from the digital signal processor based on the command to the user of a telephone wearing the hearing aid;
  receiving a response to the test tone by the user; and
  storing the response to the test tone by the user in the computer, wherein the command is generated by a first computer at a first location and is received by a second computer at a second location, and said second computer sends the command to the digital processor.

14. A method for remotely performing a hearing test on a user of a hearing aid via a telephone system, the method comprising:
  transmitting a command from a remote computer over the telephone system to a telephone of the user;
  rendering the command, by the telephone, as a sound signal;
  receiving the sound signal at the hearing aid;
  generating a test signal, by a signal processor in the hearing aid, based on the sound signal;
  generating a test tone, by the hearing aid, based on the test signal;
  transmitting a user response to the test tone to the remote computer; and
  generating, by the remote computer, hearing test results for the user of the hearing aid based on the user response.

15. The method of claim 14, wherein:
the command is a DTMF signal.

16. The method of claim 14, further comprising:
generating adjustments, at the remote computer, for the hearing aid based on the hearing test results; and
transmitting the adjustments from the remote computer to the hearing aid to adjust operations of the hearing aid.

17. The method of claim 16, wherein:
generating the adjustments comprises retrieving an audiogram from memory at the remote computer based on the hearing test results; and
transmitting the audiogram to the hearing aid.

18. The method of claim 16, wherein:
the adjustments are transmitted from the remote computer to the telephone via the telephone system; and
the adjustments are transmitted from the telephone to the hearing aid as sound signals.

19. The method of claim 14, wherein the user response is entered by the user using a key pad on the telephone and transmitted to the remote computer via the telephone system.

20. The method of claim 14, wherein the user response is entered by the user into a local computer and transmitted from the local computer to the remote computer.

21. The method of claim 14, wherein the signal processor is a digital signal processor.

22. A hearing aid, comprising a signal processor, adapted to support remote performance of a hearing test on a user of the hearing aid via a telephone system, wherein:
the hearing aid is adapted to receive a sound signal from a telephone, the sound signal corresponding to a command transmitted from a remote computer over the telephone system to the telephone of the user, wherein the telephone rendered the command as the sound signal;
the signal processor is adapted to generate a test signal based on the sound signal;
the hearing aid is adapted to generate a test tone based on the test signal, wherein a user response to the test tone is transmitted to the remote computer, which generates hearing test results for the user of the hearing aid based on the user response.

23. The hearing aid of claim 22, wherein:
the command is a DTMF signal.

24. The hearing aid of claim 22, wherein the hearing aid is adapted to receive adjustments generated at the remote computer based on the hearing test results, wherein the adjustments adjust operations of the hearing aid.

25. The hearing aid of claim 24, wherein the adjustments comprise an audiogram retrieved from memory at the remote computer based on the hearing test results and transmitted to the hearing aid.

26. The hearing aid of claim 24, wherein:
the adjustments are transmitted from the remote computer to the telephone via the telephone system; and
the adjustments are transmitted from the telephone to the hearing aid as sound signals.

27. The hearing aid of claim 22, wherein the user response is entered by the user using a key pad on the telephone and transmitted to the remote computer via the telephone system.

28. The hearing aid of claim 22, wherein the user response is entered by the user into a local computer and transmitted from the local computer to the remote computer.

29. The hearing aid of claim 22, wherein the signal processor is a digital signal processor.

30. A remote computer adapted to support remote performance of a hearing test on a user of a hearing aid via a telephone system, wherein the remote computer is adapted to:
transmit a command over the telephone system to a telephone of the user, wherein:
the telephone renders the command as a sound signal;
the hearing aid receives the sound signal;
a signal processor in the hearing aid generates a test signal based on the sound signal;
the hearing aid generates a test tone based on the test signal;
receive a user response to the test tone; and
generate hearing test results for the user of the hearing aid based on the user response.

31. The remote computer of claim 30, wherein:
the command is a DTMF signal.

32. The remote computer of claim 30, wherein the remote computer is adapted to:
generate adjustments based on the hearing test results; and
transmit the adjustments to the hearing aid, wherein the adjustments adjust operations of the hearing aid.

33. The remote computer of claim 32, wherein the adjustments comprise an audiogram retrieved from memory at the remote computer based on the hearing test results and transmitted to the hearing aid.

34. The remote computer of claim 32, wherein:
the remote computer is adapted to transmit the adjustments to the telephone via the telephone system; and
the adjustments are transmitted from the telephone to the hearing aid as sound signals.

35. The remote computer of claim 30, wherein:
the user response is entered by the user using a key pad on the telephone; and
the remote computer is adapted to receive the user response via the telephone system.

36. The remote computer of claim 30, wherein:
the user response is entered by the user into a local computer; and
the remote computer is adapted to receive the user response from the local computer.

37. The remote computer of claim 30, wherein the signal processor is a digital signal processor.

38. A system for remotely performing a hearing test on a user of a hearing aid via a telephone system, the system comprising the hearing aid and a remote computer, wherein:
the remote computer is adapted to transmit a command over the telephone system to a telephone of the user, wherein the telephone renders the command as a sound signal;
the hearing aid is adapted to receive the sound signal;
a signal processor in the hearing aid is adapted to generate a test signal based on the sound signal;
the hearing aid is adapted to generate a test tone based on the test signal;
the remote computer is adapted to receive a user response to the test tone; and
the remote computer is adapted to generate hearing test results for the user of the hearing aid based on the user response.

39. The system of claim 38, wherein:
the command is a DTMF signal.

40. The system of claim 38, wherein:
the remote computer is adapted to generate adjustments for the hearing aid based on the hearing test results; and the remote computer is adapted to transmit the adjustments to the hearing aid to adjust operations of the hearing aid.

41. The system of claim 40, wherein the remote computer is adapted to:
generate the adjustments by retrieving an audiogram from memory at the remote computer based on the hearing test results; and
transmit the audiogram to the hearing aid.

42. The system of claim 40, wherein:
the remote computer is adapted to transmit the adjustments to the telephone via the telephone system; and
the adjustments are transmitted from the telephone to the hearing aid as sound signals.

43. The system of claim 38, wherein:
the user response is entered by the user using a key pad on the telephone; and
the remote computer is adapted to receive the user response via the telephone system.

44. The system of claim 38, wherein:
the user response is entered by the user into a local computer; and
the remote computer is adapted to receive the user response from the local computer.

45. The system of claim 38, wherein the signal processor is a digital signal processor.

* * * * *